(12) United States Patent
Warren et al.

(10) Patent No.: US 10,149,068 B2
(45) Date of Patent: Dec. 4, 2018

(54) HEARING PROSTHESIS SOUND PROCESSING

(71) Applicant: Cochlear Limited, Macquarie University (AU)

(72) Inventors: Chris Warren, Beecroft (AU); Naomi Croghan, Denver, CO (US)

(73) Assignee: Cochlear Limited, Macquarie University (AU)

( * ) Notice: Subject to any disclaimer, the term of this patent is extended or adjusted under 35 U.S.C. 154(b) by 0 days.

(21) Appl. No.: 15/165,483

(22) Filed: May 26, 2016

(65) Prior Publication Data

US 2017/0064462 A1    Mar. 2, 2017

Related U.S. Application Data

(60) Provisional application No. 62/209,599, filed on Aug. 25, 2015.

(51) Int. Cl.
*A61N 1/36* (2006.01)
*H04R 25/00* (2006.01)

(52) U.S. Cl.
CPC ....... *H04R 25/353* (2013.01); *A61N 1/36036* (2017.08)

(58) Field of Classification Search
None
See application file for complete search history.

(56) References Cited

U.S. PATENT DOCUMENTS

| | | | |
|---|---|---|---|
| 9,008,339 B1* | 4/2015 | Bacon | H04R 25/353 381/312 |
| 2006/0287690 A1 | 12/2006 | Bouchataoui et al. | |
| 2008/0234783 A1 | 9/2008 | Van Den Honert | |
| 2010/0027821 A1 | 2/2010 | Fischer et al. | |
| 2011/0004273 A1 | 1/2011 | Van den Heuvel et al. | |
| 2011/0028777 A1* | 2/2011 | Rastatter | A61F 5/58 600/23 |

(Continued)

FOREIGN PATENT DOCUMENTS

KR  1020100122001    11/2010
WO  WO2014114337 A1    7/2014

OTHER PUBLICATIONS

PCT International Search Report; International application No. PCT/IB2016/055057, 3 pages.

(Continued)

*Primary Examiner* — Ankit D Tejani
(74) *Attorney, Agent, or Firm* — Edell, Shapiro & Finnan, LLC (57) ABSTRACT

A method may include receiving a sound signal and identifying a plurality of components of the sound signal. The plurality of components may include a tonal component and an atonal component. The method may further include generating a first stimulation signal based on the tonal component of the sound signal, wherein the first stimulation signal is configured for application by a first stimulator to provide an acoustic output from a hearing prosthesis system. In addition, the method may include generating a second stimulation signal based on the atonal component of the sound signal, wherein the second stimulation signal is configured for application by a second stimulator to provide an electrical output from the hearing prosthesis system.

20 Claims, 6 Drawing Sheets

(56) References Cited

U.S. PATENT DOCUMENTS

| | | |
|---|---|---|
| 2011/0280427 A1 | 11/2011 | Buyens |
| 2012/0215057 A1* | 8/2012 | Parker ................. H04R 25/606 600/25 |
| 2013/0197606 A1* | 8/2013 | Litvak ................ A61N 1/36032 607/57 |
| 2014/0105434 A1* | 4/2014 | Goorevich ......... A61N 1/36032 381/320 |
| 2015/0016614 A1 | 1/2015 | Buyens |

OTHER PUBLICATIONS

PCT Written Opinion of the International Searching Authority, PCT/IB2016/055057, 6 pages.

* cited by examiner

HEARING PROSTHESIS SOUND PROCESSING

CROSS-REFERENCE TO RELATED APPLICATION

This application claims priority to U.S. Provisional Patent Application No. 62/209,599 filed on Aug. 25, 2015, the entirety of which is incorporated herein by reference.

BACKGROUND

Various types of hearing prostheses provide persons with different types of hearing loss with the ability to perceive sound. Generally, hearing loss may be conductive, sensorineural, or some combination of both conductive and sensorineural. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural signals, or any other part of the ear, auditory nerve, or brain that may process the neural signals.

Example hearing prostheses include traditional hearing aids, vibration-based hearing devices, cochlear implants, and auditory brainstem implants. A traditional hearing aid, which is an acoustic stimulation device, typically includes a small microphone to detect sound, an amplifier to amplify certain portions of the detected sound, and a speaker to transmit the amplified sounds into the person's ear canal.

Vibration-based hearing devices, which are also acoustic stimulation devices, typically include a microphone to detect sound and a vibration mechanism to apply vibrations corresponding to the detected sound directly to a person, thereby causing vibrations in the person's inner ear. Vibration-based hearing devices include, for example, bone conduction devices, direct acoustic cochlear stimulation devices, or other vibration-based devices. A bone conduction device transmits vibrations corresponding to sound via the teeth and/or skull. A so called middle ear device transmits vibrations corresponding to sound via the middle ear (i.e., the ossicular chain), without using the teeth or skull. A direct acoustic cochlear stimulation device transmits vibrations corresponding to sound via the inner ear (i.e., the cochlea), without using the teeth, skull or middle ear.

Cochlear implants can provide a person with the ability to perceive sound by stimulating the person's auditory nerve via an array of electrodes implanted in the person's cochlea. A microphone coupled to the cochlear implant detects sound waves, which are converted into a series of electrical stimulation signals that are delivered to the implant recipient's cochlea via the array of electrodes. Auditory brainstem implants can use technology similar to cochlear implants, but instead of applying electrical stimulation to a person's cochlea, auditory brainstem implants apply electrical stimulation directly to a person's brain stem, bypassing the cochlea altogether. Electrically stimulating auditory nerves in a cochlea with a cochlear implant or electrically stimulating a brainstem may enable persons with hearing loss to perceive sound.

Further, some persons may benefit from a hearing prosthesis that combines two or more characteristics of the traditional hearing aids, vibration-based hearing devices, cochlear implants, or auditory brainstem implants (e.g., two or more modes of stimulation) to enable the person to perceive sound. Such hearing prostheses can be referred to as bimodal hearing prostheses. Still other persons benefit from two hearing prostheses, one for each ear (e.g., a so called binaural system generally or a bilateral system for persons with two cochlear implants).

SUMMARY

Sound processing strategies for hearing prostheses have tended to focus on speech, as it is the most important aspect for the typical user. However, it is also important to provide satisfactory performance for other sounds, such as music. Applying conventional speech processing strategies to music may not produce a satisfactory result. For speech, relatively little information is required to enable at least a degree of understanding. In contrast, music may have many simultaneous elements, all of which may interact to produce a harmonious whole. This complexity of music may not be fully reproduced by conventional speech processing strategies, and the result of applying such an approach to music may not create a satisfactory percept for users. Accordingly, it is generally desirable to develop a sound processing strategy that provides improved perception of music for users of hearing prostheses.

The present disclosure relates to processing of sound signals that represent, at least in part, music. The processing of the sound signals generates a stimulation signal representative of the sound signal, and the present disclosure relates to generating stimulation signals that improve the perception of music (as compared to using conventional speech processing strategies to process music) when the stimulation signals are applied by a hearing prosthesis system to a recipient or user.

In one example, one or more microphones of a hearing prosthesis system receive sound signals. These received sound signals represent, at least in part, music from a music source (e.g., a stereo connected to speakers, a CD player connected to speakers, live music, or the like). The microphone then provides the sound signals (either directly or indirectly) to a sound processor of the hearing prosthesis system. Alternatively or in addition, the sound processor of the hearing prosthesis system may receive the sounds signals as a direct audio input via some wired or wireless coupling to a music source.

According to one aspect of the present disclosure, the sound processor identifies one or more components of the sound signal, such as one or more of tonal components, atonal components, definite pitch components, and/or indefinite pitch components. The sound processor may then generate stimulation signals based on the identified components. For instance, the sound processor may generate a first stimulation signal based on the tonal components and/or definite pitch components, and the first stimulation signal may be configured for application by a first stimulator to provide an acoustic output from the hearing prosthesis system. Further, the sound processor may generate a second stimulation signal based on the atonal components and/or indefinite pitch components, and the second stimulation signal may be configured for application by a second stimulator to provide an electrical output from the hearing prosthesis system.

The preceding paragraph describes a so called real-time processing example. For instance, identification of atonal components occurs just before a corresponding stimulation signal serves as the basis for an output from the hearing prosthesis system. The components are not stored in anything more than a transient manner. In another example, the sound processor may "pre-process" the sound signals to identify the components of the sound signal and to generate the stimulation signals. In this "pre-processed" example, the sound processor may store the identified components or otherwise identify these components as different components or tracks, and/or the sound processor may store the generated stimulation signals as MP3 files on a music player or other storage device for later retrieval and application by one or more stimulators.

According to another aspect, the sound processor may process one or more components of the sound signal by transposing component(s) or a portion thereof to a different frequency range. For instance, the sound processor may process one or more components of the sound signal by transposing a portion of the component(s) that are above a given frequency to a frequency range below the given frequency. In another example, the sound processor may process one or more of the tonal components or definite pitch components that are above the given frequency to a frequency range below the given frequency. In yet another example, the sound processor may process one or more low-frequency percussion sounds that are below the given frequency to a frequency range above the given frequency.

Various aspects and examples are described herein as being implemented by methods, systems (such as, a hearing prosthesis system and/or a separate sound processor), and/or programming in the form of a non-transitory computer-readable medium for processing music.

DETAILED DESCRIPTION

The following detailed description describes various features, functions, and attributes with reference to the accompanying figures. In the figures, similar symbols typically identify similar components, unless context dictates otherwise. The illustrative embodiments described herein are not meant to be limiting. Certain features, functions, and attributes disclosed herein can be arranged and combined in a variety of different configurations, all of which are contemplated in the present disclosure.

For illustration purposes, various examples are described herein with respect to a bimodal electrical-acoustic hearing prosthesis that includes electrical stimulation components and acoustic stimulation components. An example of a bimodal electrical-acoustic hearing prosthesis described includes cochlear implant components that provide electrical stimulation and traditional hearing aid components that provide acoustic stimulation. However, various features and functions disclosed herein are also applicable to other types of bimodal devices as well as bilateral and binaural systems that include both electrical stimulation and acoustic stimulation.

A typical recipient of a bimodal prosthesis has sensorineural hearing loss that affects a higher frequency range more severely and may maintain some useful lower frequency range hearing. Thus, a sound processing strategy for speech may include cochlear implant components to deliver sound through electrical stimulation signals for the higher frequency range and traditional hearing aid components to deliver sound through acoustic stimulation signals for the lower frequency range. This is generally an effective sound processing strategy for speech. However, for music, this may not be a complete or effective sound processing strategy (or at least it may be possible to make improvements in the sound processing of music), because, in part, the electrical stimulation components may have a limited ability to encode pitch and other musical information or signals. As will be discussed in more detail hereinafter, the present disclosure provides a sound processing strategy for music that identifies and/or separates certain musical components from a received sound signal and processes these musical components to improve the perception of the music by a recipient of a hearing prosthesis.

Figure 1:
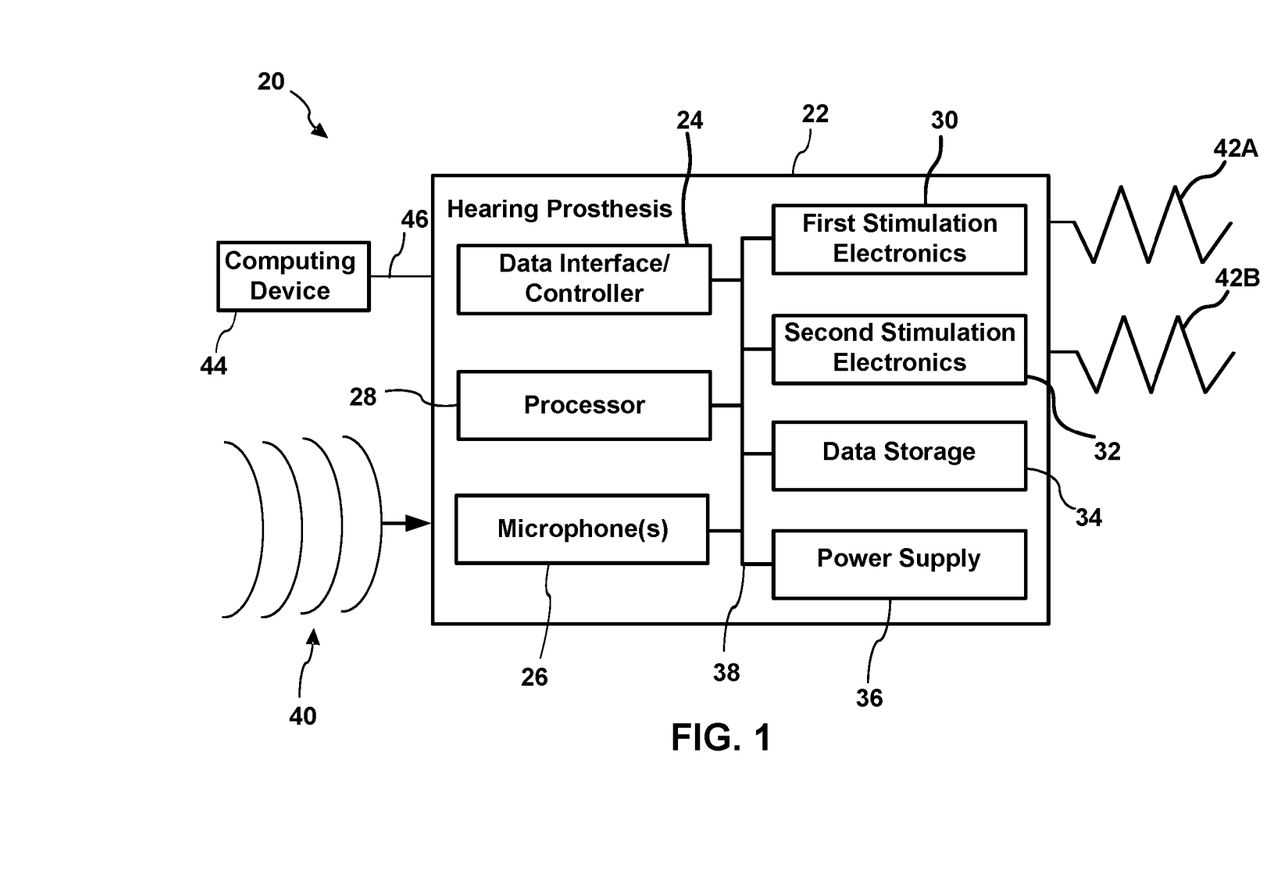
FIG. 1 illustrates a block diagram of a hearing prosthesis system according to an embodiment of the present disclosure.

Referring now to FIG. 1, an example hearing prosthesis system 20 includes a bimodal hearing prosthesis 22. In the present example, the bimodal hearing prosthesis 22 includes components to apply more than one form of stimulation. For instance, the bimodal hearing prosthesis 22 can include components of a cochlear implant, a traditional hearing aid, a bone conduction device, a direct acoustic cochlear stimulation device, an auditory brainstem implant, or any other type of hearing prosthesis configured to assist a prosthesis recipient in perceiving sound.

The hearing prosthesis 22 illustrated in FIG. 1 includes a data interface or controller 24 (such as a universal serial bus (USB) controller), one or more microphones 26, one or more processors 28 (such as digital signal processors (DSPs)), first stimulation electronics 30, second stimulation electronics 32, data storage 34, and a power supply 36 all of which are illustrated as being coupled directly or indirectly via a wired or wireless link 38. In one non-limiting example, the first stimulation electronics 30 include acoustic stimulation electronics, such as hearing aid components, for providing acoustic stimulation to a recipient, and the second stimulation electronics 32 include electrical stimulation electronics, such as cochlear implant components, for providing electrical stimulation to the recipient.

Generally, the microphone(s) 26 are configured to receive external acoustic or sound signals 40. The microphone(s) 26 can include combinations of one or more omnidirectional or directional microphones that are configured to receive background sounds and/or to focus on sounds from a specific direction, such as generally in front of the prosthesis recipient. Alternatively or in conjunction, the hearing prosthesis 22 is configured to receive sound information from other sources, such as sound information received through the controller 24 from an external source.

The processor 28 is configured to process, amplify, encode, or otherwise convert the acoustic signals 40 into stimulation data that are provided to the acoustic and electrical stimulation electronics 30, 32. The acoustic and electrical stimulation electronics 30, 32 can then apply the stimulation data to the recipient as output stimulation signals 42 to allow the recipient to perceive the original external acoustic signals 40 as sound. More particularly, in the context of the present bimodal hearing prosthesis 22, the acoustic signals 40 are converted into acoustic stimulation data and electrical stimulation data. The acoustic stimulation data are provided to the acoustic stimulation electronics 30 to apply acoustic output stimulation signals 42A to the recipient. The electrical stimulation data are provided to the electrical stimulation electronics 32 to apply electrical output stimulation signals 42B to the recipient.

The processor 28 converts the external acoustic signals 40 into the stimulation data in accordance with configuration settings or data for a prosthesis recipient. Generally, the configuration settings allow a hearing prosthesis to be configured for or fitted to a particular recipient. More particularly, in the present example, the bimodal hearing prosthesis 22 can be programmed with configuration settings that include acoustic stimulation configuration settings for generating the acoustic stimulation data and electrical stimulation configuration settings for generating the electrical stimulation data. These configuration settings can be stored in the data storage 34.

Illustratively, the electrical stimulation configuration settings include sound processing strategies that are implemented by the processor 28 to generate the electrical stimulation data from the acoustic signals 40. For electrical stimulation data that are applied to cochlear implant components and, more particularly, to a cochlear electrode array implanted in a recipient, the stimulation data can define one or more of an intended electrode, mode of stimulation, stimulation amplitude, and stimulation duration. Thus, the electrical stimulation data can be used to control the timing and intensity of auditory stimulation pulses that are applied to a recipient by the stimulation electronics 32.

Generally, speech algorithms include, but are not limited to, Continuous Interleaved Sampling (CIS), Spectral PEAK Extraction (SPEAK), Advanced Combination Encoders (ACE), Fundamental Asynchronous Stimulus Timing (FAST), Simultaneous Analog Stimulation, MPS, Paired Pulsatile Sampler, Quadruple Pulsatile Sampler, Hybrid Analog Pulsatile, n-of-m, and HiRes. More particularly, SPEAK is a low rate strategy that can operate within the 250-500 Hz range, and ACE is a combination of CIS and SPEAK. Other proprietary and non-proprietary speech algorithms are also possible. The operation of these algorithms provides information on a stimulation mode (e.g., monopolar or bipolar channel), a target electrode(s), and an amplitude of stimulation pulse(s), for example.

Referring again to the acoustic stimulation configuration settings, these settings include prescription rules for defining parameters, such as gain and maximum power output (MPO) levels or settings, from the hearing prosthesis recipient's audiogram and maximum comfort levels across a range of frequencies for acoustic stimulation. Generally, the audiogram is a graph of the audible thresholds for a range of frequencies. In some cases, the audiogram is defined by measured threshold levels across the recipient's residual hearing range. If a recipient specific audiogram is unavailable, a population average audiogram can also be used with the prescription rule to fit traditional hearing aid components of the bimodal hearing prosthesis 22. In the present example, the prescription rule can also be applied to the audiogram to set a cross-over frequency between the acoustic stimulation and the electrical stimulation.

Generally, prescription rules are mathematical models or algorithms for calculating optimal gain settings so that external sounds are perceived by a hearing prosthesis recipient intelligibly and at similar loudness that the external sounds would be perceived by a normal-hearing person. Prescription rules typically focus on making speech intelligible and reducing background noise. Some prescription rules are non-linear and apply different gain settings for different frequencies or frequency bands to provide a more fine-tuned hearing prosthesis fitting for the recipient. Example prescription rules include, but are not limited to, National Acoustic Laboratories' (NAL) prescriptions rules (including NAL-R, NAL-RP, NAL-NL2, etc.), the Desired Sensation Level (DSL) prescription rule, and the Cochlear Hybrid Prescription Rule (CHP). Other proprietary and non-proprietary prescription rules are also possible.

As discussed generally above, the first stimulation electronics 30 can include traditional hearing aid components, such as a small speaker or earphone, and the second stimulation electronics 32 can include cochlear implant components, such as an electrode array. In other non-limiting examples, the stimulation electronics 30, 32 can include components for a bone conduction device, a middle ear device, a direct acoustic cochlear stimulation device, and/or an auditory brain stem implant.

Referring back to the power supply 36, this power supply provides power to various components of the hearing prosthesis 22. The power supply 36 can be any suitable power supply, such as non-rechargeable or rechargeable batteries. In one example, the power supply 36 is a battery that can be recharged wirelessly, such as through inductive charging. Such a wirelessly rechargeable battery facilitates complete subcutaneous implantation of the prosthesis 22 to provide a fully or at least partially implantable prosthesis. A fully implanted hearing prosthesis has the added benefit of enabling the recipient to engage in activities that expose the recipient to water or high atmospheric moisture, such as swimming, showering, saunaing, etc., without the need to remove, disable or protect, such as with a water/moisture proof covering or shield, the hearing prosthesis. A fully implanted hearing prosthesis also spares the recipient of stigma, imagined, or otherwise, associated with use of the prosthesis.

Referring again to the data storage 34, this component generally includes any suitable volatile and/or non-volatile storage components. Further, the data storage 34 may include computer-readable program instructions and perhaps additional data. In some embodiments, the data storage 34 stores data and instructions used to perform at least part of the herein-described methods and processes and/or at least part of the functionality of the systems described herein. Although, the data storage 34 in FIG. 1 is illustrated as a separate block, in some embodiments, the data storage can be incorporated into other components of the prosthesis 22, such as the processor 28.

The system 20 illustrated in FIG. 1 further includes a computing device 44 that is configured to be communicatively coupled to the hearing prosthesis 22 via a connection or link 46. The link 46 may be any suitable wired connection, such as an Ethernet cable, a Universal Serial Bus connection, a twisted pair wire, a coaxial cable, a fiber-optic link, or a similar physical connection, or any suitable wireless connection, such as BLUETOOTH, WI-FI, WiMAX, inductive or electromagnetic coupling or link, and the like.

In general, the computing device 44 and the link 46 are used to operate the hearing prosthesis 22 in various modes. In one example, the computing device 44 and the link 46 are used to adjust various parameters of the bimodal hearing prosthesis 22. The computing device 44 and the link 46 can also be used to load a recipient's configuration settings on the hearing prosthesis 22 such as via the data interface 24. In another example, the computing device 44 and the link 46 are used to upload other program instructions and firmware upgrades to the hearing prosthesis 22. In yet other examples, the computing device 44 and the link 46 are used to deliver data (e.g., sound information) and/or power to the hearing prosthesis 22 to operate the components thereof and/or to charge the power supply 36. Still further, various other modes of operation of the prosthesis 22 can be implemented by utilizing the computing device 44 and the link 46.

The computing device 44 can further include various additional components, such as a processor, a storage device, and a power source. Further, the computing device 44 can include user interface or input/output devices, such as buttons, dials, a touch screen with a graphic user interface, and the like, that can be used to turn the prosthesis 22 on and off, adjust the volume, adjust or fine tune the configuration data or parameters, etc. Thus, the computing device 44 can be utilized by the recipient or a third party, such as a guardian of a minor recipient or a health care professional, to control or adjust the hearing prosthesis 22.

Various modifications can be made to the system 20 illustrated in FIG. 1. For example, user interface or input/output devices can be incorporated into the hearing prosthesis 22, instead of or in combination with the user interface or input/output devices of the computing device 44. Further, the system 20 may include additional or fewer components arranged in any suitable manner.

Additionally, depending on the type and design of the system 20, the illustrated components may be enclosed within a single operational unit or distributed across multiple operational units, for example, two or more internal units, two or more external units and an internal unit, and so on. Generally, an internal unit can be hermetically sealed and adapted to be at least partially implanted in a recipient. Indeed, in some embodiments, all of the components of hearing prosthesis system 20, with the exception of computing device 44, are implanted in the recipient to form a totally implanted hearing prosthesis or system.

Figure 2:
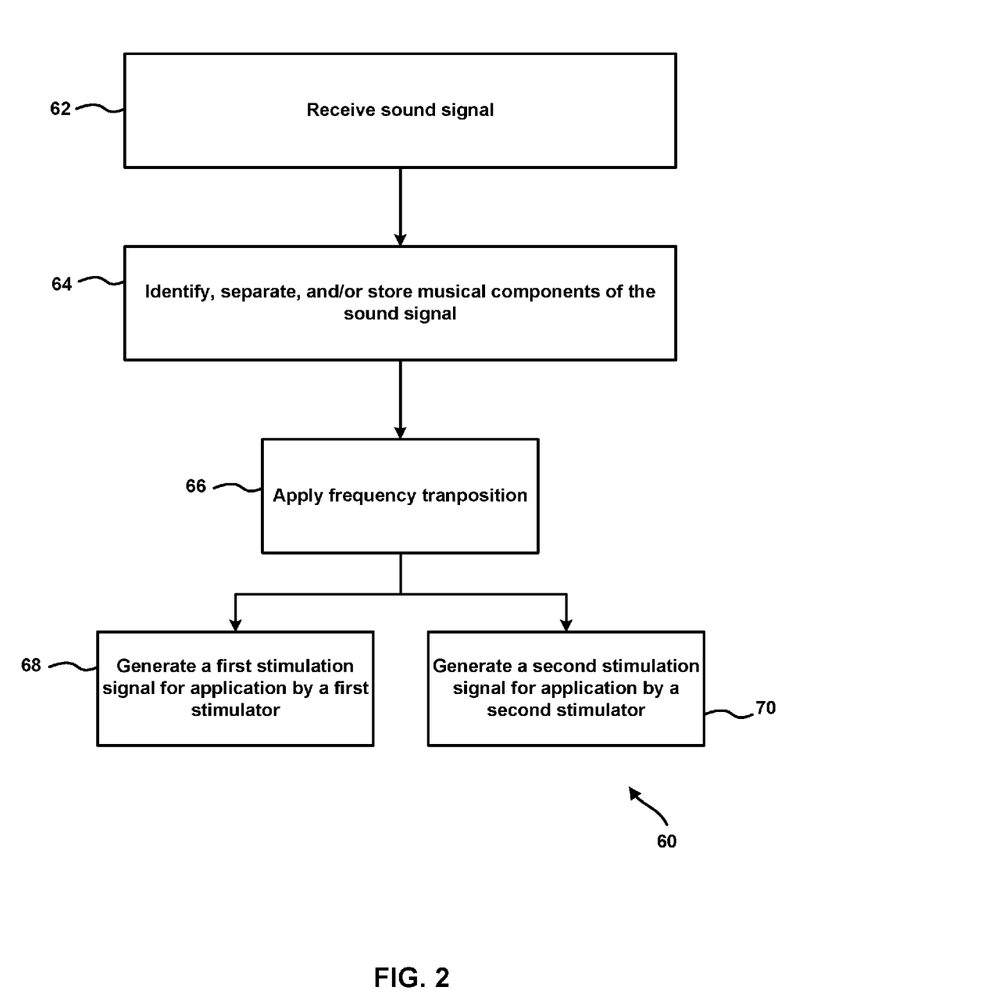
FIG. 2 is a flowchart showing a method or algorithm for controlling a bimodal hearing prosthesis.

Referring now to FIG. 2, an example method 60 is illustrated, which can be implemented by the systems and devices described herein. Generally, the method 60 may include one or more operations, functions, or actions as illustrated by one or more of blocks 62-70. Although the blocks 62-70 are illustrated in a particular order, these blocks may also be performed in a different order than illustrated, and some blocks may even be omitted or added according to certain implementations.

In addition, each block 62-70 may represent a module, a segment, or a portion of program code, which includes one or more instructions executable by a processor for implementing specific logical functions or steps in the process. The program code may be stored on any type of computer readable medium or storage device including a disk or hard drive, for example. The computer readable medium may include non-transitory computer readable medium, such as computer-readable media that stores data for short periods of time like register memory, processor cache, and Random Access Memory (RAM). The computer readable medium may also include non-transitory media, such as secondary or persistent long term storage, like read only memory (ROM), optical or magnetic disks, compact-disc read only memory (CD-ROM), etc. The computer readable media may also include any other volatile or non-volatile storage systems. The computer readable medium may be considered a computer readable storage medium, for example, or a tangible storage device. In addition, one or more of the blocks 62-70 may represent circuitry that is wired to perform the specific logical functions of the method 60.

In FIG. 2, at block 62, a device or system, such as the system 20, the hearing prosthesis 22, the computing device 44, or some other computing device, receives a sound signal. In one example, one or more microphones of a hearing prosthesis system may receive sound signals, and these received sound signals may represent, at least in part, music from a music source (e.g., a stereo system, CD player, live music, or the like). The microphone then provides the sound signals (either directly or indirectly) to a sound processor of the hearing prosthesis system (e.g., processor 28). Alternatively or in addition, at block 62, the sound processor of the hearing prosthesis system may receive the sounds signals as a direct audio input.

At block 64, the sound processor identifies one or more components of the sound signal, such as one or more of tonal components, atonal components, definite pitch components, indefinite pitch components, harmonic components, inharmonic components, melodic components, non-melodic components, and/or components that correspond to one or more instruments. At block 64, the sound processor may also separate and/or store the identified musical components of the sound signal. The sound processor may use music processing software known by those in the field of music processing to identify different components of the sound signal.

Generally, tonal sounds relate to a tonic, key, or tonal center of a musical composition. In one example, tonal sounds relate to the tonic or tonal center by corresponding to notes in a scale defined by the tonic or key. Atonal sounds generally lack such a relation to the tonal center or key. Tonal sounds are commonly considered to have a definite pitch, while atonal sounds are commonly considered to have an indefinite pitch. In some cases, however, atonal sounds are considered to have a definite pitch (e.g., a spoken voice may have a definite pitch represented by a fundamental frequency of the voice, but may still be atonal because the spoken voice does not necessarily fit within a musical key).

Further, pitches may generally refer to a perceptual ordering of sounds on a frequency-related scale. A particular pitch relates to a position of a single sound in the range or scale. Pitch and tone may be related in that a tone represents the "quality" of a sound, such as how shrill or full an audible pitch sounds. A note is a named pitch. For instance, Western music generally refers to the 440 Hz pitch as "A" (more specifically, A4).

A typical normal-hearing listener can possibly or relatively easily identify the pitch of a sound or note that is considered to have a definite pitch. A computing device, such as a sound processor, may be configured to identify a sound with a definite pitch by identifying harmonic (or near harmonic) characteristics of the sound. Harmonic sound characteristics may include multiple sound frequencies, of which higher sound frequencies are approximately integer multiples of a lowest sound frequency (or fundamental frequency). In one example, at block 64 the sound processor identifies a definite pitch component of the sound signal by identifying a fundamental frequency of the sound signal that also has an amplitude greater than a predetermined threshold.

In contrast, any listener may find it impossible or relatively difficult to identify the pitch of a sound or note that is considered to have an indefinite pitch. A computing device, such as a sound processor, may be configured to identify a sound with an indefinite pitch by determining that the sound does not have harmonic (or near harmonic) characteristics. Such a sound may be considered to have inharmonic characteristics, for example, by including multiple sound frequencies that depart from the integer multiple relationship of harmonic sounds.

A computing device may also be configured to identify a sound with an indefinite pitch by determining that the sound lacks a strong fundamental frequency having an amplitude greater than a predetermined threshold, such that the sound does not produce a sensation of pitch.

In an example, a computing device is configured to identify an atonal sound by determining that the sound does include a strong fundamental frequency or recognizable pitch, but that the recognizable pitch is unrelated to the larger musical composition. For example, a sound that does have a recognizable pitch may be atonal if the sound does not relate to a key or melody of the musical composition.

At block 64, the sound processor may also identify other musical components, such as sounds corresponding to percussion instruments. Generally, percussion instruments include instruments that make a sound when the instrument is hit, shaken, scraped, or the like. Some percussion instruments, such as a xylophone, timpani, or piano, are tuned and can produce sounds with definite pitches. Other percussion instruments, such as a bass drum, tambourine, cymbals, maracas, or castanets, are not tuned, may be atonal, and may generally have an indefinite pitch. In one example, the sound processor identifies percussion instruments by detecting transient signal characteristics, such as a fast rise and fall or release.

The sound processor may also identify musical components that correspond to other instruments, such as a guitar, a bass, a violin, a piano, a human voice, and a multitude of other instruments. The human voice, and other instruments, may generally correspond to tonal or definite pitch components of a musical composition. In an example, a computing device is configured to analyze a modulation spectrum of received sound signals and/or other characteristics of the sound signals to identify characteristics that are associated with different instruments. For instance, the human voice is generally associated with a particular modulation rate based on syllabic structure (e.g., a spoken human voice has a distinctive modulation frequency of about 4 Hz). In one example, the sound processor detects modulation frequencies that are around 4 Hz to identify a spoken human voice, which may be common to certain types of music. A percussion instrument (such as most drums) may be associated with a different rate of modulation and also a quick attack and release characteristic. Another technique for isolating instruments is to use an adjustable narrowband filter to segregate components in the frequency domain.

In a further example, the sound processor identifies spatial locations represented in the received sound signal to identify different instruments. For instance, the sound processor may identify the human voice as being around a spatial center of the received sound signal. In another example, the sound processor identifies signal characteristics related to a spectral shape/tilt/centroid as being associated with different instruments.

Additional details regarding processing music for a hearing prosthesis are disclosed in U.S. Patent Application Publication No. 2011/0280427 filed on Jun. 17, 2011, U.S. Patent Application Publication No. 2015/0016614 filed on Jul. 11, 2014, the contents of each of which are incorporated herein by reference.

Further, at block 64 the sound processor may also identify melodic and/or harmonic musical components. Generally, a melody of a musical composition is an organized arrangement of tones (or pitches or notes) using a recognized scale, stressing particular tones and using specific configurations of intervals between tones. In music, harmony generally relates to the sound of two or more notes heard simultaneously.

In the present example, at block 66, the sound processor applies frequency transposition to one or more of the identified musical components. More particularly, the sound processor processes one or more components of the sound signal to identify one or more portions thereof that are above a given frequency, and transposes or shifts the portion(s) of the component(s) that are above the given frequency to a frequency range below the given frequency. For instance, the sound processor processes one or more of the tonal components and/or definite pitch components to segregate and transpose portions of such components that are above the given frequency to a frequency range below the given frequency.

Alternatively or in combination, the sound processor processes the sound signal to identify, segregate, and transpose one or more music components associated with specific instruments (e.g., flute, violin, piccolo, and the like). For instance, if a music component is associated with a violin and includes components that are above the given frequency, the sound processor transposes or shifts the entire music component down below the given frequency to retain musical relationships in the music component. In one example, the sound processor transposes or shifts the portions of the components lower by one or more whole octaves.

In another example, at block 66, the sound processor identifies one or more tonal components or definite pitch components that correspond to a percussion instrument (e.g., timpani drum), and segregates and transposes portions of such components that are below the given frequency to a frequency range above the given frequency. In this example, the sound processor may transpose or shift the portions of the components higher by one or more whole octaves.

Transposing the musical components by one or more whole octaves helps to retain the tonality of the musical piece (e.g., the proper harmonies and chord progressions will be maintained). One potential method of isolating instruments will be through an adjustable narrowband filter. Through segregating and transposing certain musical components of a sound signal, the present disclosure may improve music listening for hearing prosthesis recipients by exploiting the relative strength of acoustic hearing for pitch perception.

At block 66, the given frequency may be a cutoff or cross-over frequency between acoustic stimulation and electrical stimulation of a bimodal hearing prosthesis. Generally, the cutoff or cross-over frequency corresponds to the point at which residual hearing drops below about 90 dB HL on a recipient's audiogram. Illustratively, the cutoff or cross-over frequency is established during fitting of the hearing prosthesis system for a recipient. In other examples the given frequency is some other predetermined frequency. In some embodiments, the given frequency is adjustable in response to receiving an input to the hearing prosthesis system, such as a user input.

At blocks 68 and 70, the sound processor generates stimulation signals based on the identified (and optionally transposed) components. For instance, at block 68 the sound processor may generate a first stimulation signal based on the tonal components and/or definite pitch components, including transposed and/or non-transposed portions of such components. In this example, the first stimulation signal is configured for application by a first stimulator to provide an acoustic output from the hearing prosthesis system. In another example, the sound processor generates the first stimulation signal based on the whole received sound signal (e.g., a full arrangement of music).

In a further example, the sound processor generates the first stimulation signal based on definite pitch components, which helps to achieve the benefit of exploiting better pitch perception in acoustic hearing, and which may be more computationally efficient to identify, as compared to tonal components. In other examples, the sound processor generates the first stimulation signal based on melodic instrument components (e.g., violin, guitar, woodwinds, voice, and the like) that have a relationship (or that do not have a relationship) to a tonic center of a musical arrangement, or based on any sound signals with harmonic characteristics and/or fundamental frequencies that do not have transient characteristics similar to typical percussion sounds.

Further, at block 70 the sound processor generates a second stimulation signal based on the atonal components and/or indefinite pitch components, and the second stimulation signal is configured for application by a second stimulator to provide an electrical output from the hearing prosthesis system. In a further example, the sound processor generates the second stimulation signal based on indefinite pitch components, which may be more computationally efficient to identify, as compared to atonal components. In other examples, the sound processor generates the second stimulation signal based on pitched percussion instruments (e.g., a tympani), based on sound signals with both harmonic characteristics and transient characteristics, based on spoken voice or sound signals with a definite pitch that has a modulation frequency typical for speech at about 4 Hz (which may be sent to the electrical path for better speech understanding), or based on sounds signals that have transient characteristics (e.g., a quick attack and release characteristic).

The second stimulation signal may also be the whole received sound signal or a processed sound signal that is generated by extracting the tonal and/or definite pitch components from the whole received sound signal. At block 70, the sound processor processes the whole received sound signal or the processed sound signal in accordance with the typical sound processing strategy described above for bimodal hearing prosthesis to deliver sound through electrical stimulation signals for a higher frequency range above the cutoff or cross-over frequency, and to deliver sound through acoustic stimulation signals for the lower frequency range below the cutoff or cross-over frequency.

Variations of blocks 68 and 70 are also possible based on factors, such as user sound quality preference. For instance, a user or recipient of the hearing prosthesis system may prefer to have percussion or indefinite pitch components delivered through electrical stimulation signals, and the remainder of the musical sound components delivered through acoustic stimulation signals. Another user, or perhaps the same user in a different acoustic environment or listening to a different type of music, may prefer to have the entire or whole musical arrangement delivered through acoustic stimulation signals. In one example, the hearing prosthesis system described herein allows a user to toggle or switch between different variations of musical components at that delivered through acoustic and/or electrical stimulation signals. This toggling or switching may be performed during any of the blocks illustrated in FIG. 2.

After or at blocks 68 and 70, the first stimulation signal and the second stimulation signal may be stored for future use, and/or may be applied in real-time to respective first and second stimulators to allow a recipient to perceive the identified components as sound. The first and second stimulation signals may be stored in any suitable data storage, such as a data storage included with or otherwise coupled to the computing device 44, and/or the data storage 34 of the hearing prosthesis 22.

In method 60, one or more of the first or second stimulation signals may also be based on the whole or entire sound signal or on all the musical components of the sound signal. Alternatively, one or more of the first and second stimulation signals may be based on respective separated musical components of the sound signal. Thus, for example, the first stimulation signal may be based on the entire tonal component of the sound signal, and the second stimulation signal may be based on the entire atonal component of the sound signal.

A sound processor may identify the components of the sound signal and generate the stimulation signals in real-time as the sound signals are being received. In another example, music sound signals are "pre-processed" to identify different musical components of the sound signal. In this "pre-processed" example, a processor may store the identified components or otherwise identify these components as different components or tracks, and/or the processor may store the generated stimulation signals for later retrieval and application by one or more stimulators.

Figure 3:
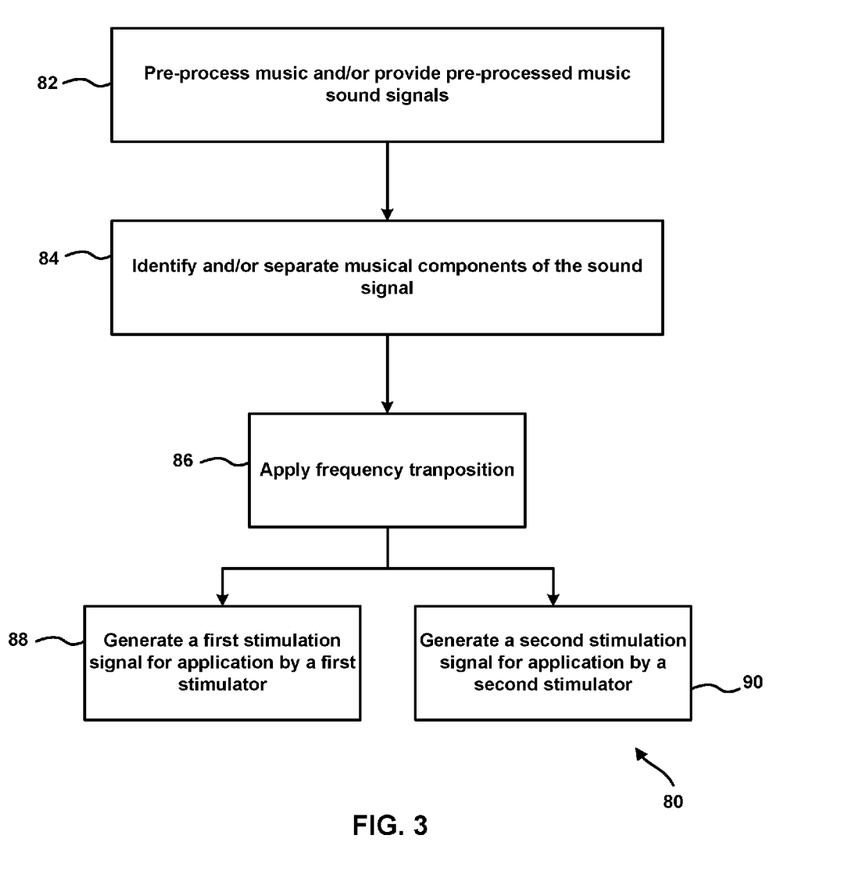
FIG. 3 is a flowchart showing another method or algorithm for controlling a bimodal hearing prosthesis.

FIG. 3 illustrates such an example method 80, which may be implemented and modified similarly to FIG. 2 described above. In method 80, at block 82, music is pre-processed (in whole or in part) to identify different musical components, such as tonal, atonal, definite pitch, indefinite pitch, different instrument components, and the like, as described herein. In one example, a musician or sound engineer uses a midi controller or something similar to identify different components, and to store the identified components or otherwise identify the components as different sound signals or tracks. For instance, for a particular popular song, the musician or sound engineer separates drum components from an original recording of the song, and replaces the drum components with one or more commands that are configured to be perceived as drums on a singular stimulator (e.g., the second stimulator described above). In another example, the musician or sound engineer removes the drum components from the original recording, and retains the drum components for presentation on a singular stimulator (e.g., the second stimulator).

In one example, at block 82, a mobile phone or other device with internal storage and an output appropriate for acoustic and electric stimulation stores the pre-processed music as separate or distinct tracks for different instruments. Instruments on these tracks may be separated at block 82 via phase cancellation and/or equalization or by creating a completely separate drum/percussion track using virtual instruments with real drum samples or by live recording the duplicate drum track. Other examples of identifying and the separating different components are also possible, such as the examples described in relation to FIG. 2.

At block 84, the pre-processed music sound signals are provided to a sound processor, which identifies and/or separates different musical components of the sound signal. The sound processor may perform some of the same processes described above in relation to block 64, however, in this example, much of the identification of different musical components has already been performed at block 82.

Thereafter, at block 86, the sound processor applies frequency transposition similarly to block 66 described above. Further, at blocks 88 and 90, the sound processor generates stimulation signals similarly to blocks 68 and 70, respectively, described above.

Figure 4:
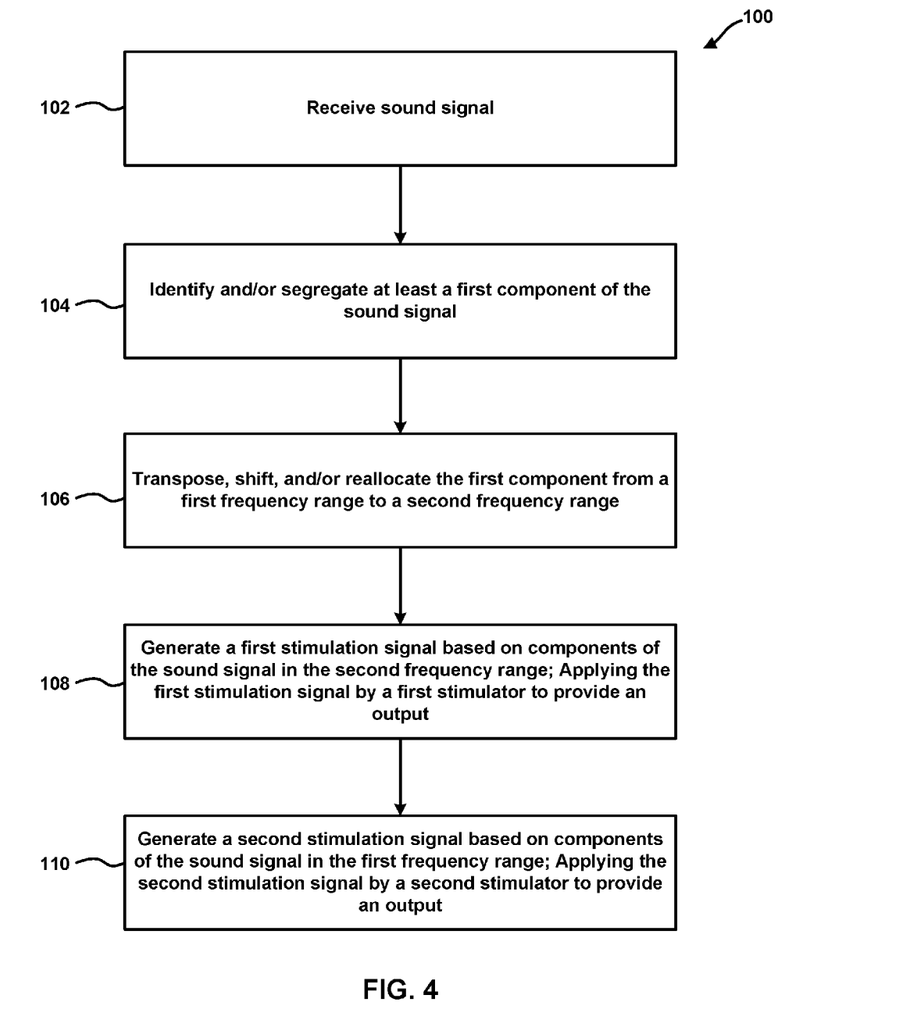
FIG. 4 is a flowchart showing another method or algorithm for controlling a bimodal hearing prosthesis.

Referring now to FIG. 4, an example method 100 is provided for applying frequency transposition to one or more components of a received sound signal. FIG. 4 may be implemented and modified similarly to FIG. 2 described above. In FIG. 4, at block 102, a sound processor receives a sound signal, which may represent music, but not necessarily. At block 104, the sound processor processes the sound signal to identify and/or segregate one or more portions or components thereof (e.g., a first component). In one example, the first component includes or consists of components that are above a given frequency.

At block 106, the sound processor performs one or more of transposition, shifting, or reallocation of the first component from a first frequency range to a second frequency range. In one example, the first frequency range is at least in part above the given frequency and includes the original first component, and the second frequency range is at least in part below the given frequency. In another example, the first frequency range is entirely above the given frequency and/or the second frequency range is entirely below the given frequency. At block 106, the given frequency may be a cutoff or cross-over frequency between acoustic stimulation and electrical stimulation of a bimodal hearing prosthesis. Generally, the cutoff or cross-over frequency corresponds to the point at which residual hearing drops below about 90 dB HL on a recipient's audiogram. Illustratively, the cutoff or cross-over frequency is established during fitting of the hearing prosthesis system for a recipient. In other examples the given frequency is some other predetermined frequency. In some embodiments, the given frequency is adjustable in response to receiving an input to the hearing prosthesis system, such as a user input.

At block 108, the sound processor generates first stimulation signals based on the components of the sound signal in the second frequency range. In one example, the sound processor generates the first stimulation signals based exclusively on the components of the sound signal in the second frequency range. These components include the first component from block 104. In one example, at block 108, a first stimulator applies the first stimulation signals to provide an output from the hearing prosthesis system. For example, the first stimulator is an acoustic stimulator.

At block 110, the sound processor generates second stimulation signals based on the components of the sound signal in the first frequency range. In one example, the sound processor generates the second stimulation signals based exclusively on the components of the sound signal in the first frequency range. In the present example, at block 110, a second stimulator applies the second stimulation signals to provide an output from the hearing prosthesis system. For example, the second stimulator is an electrical stimulator.

Figure 5:
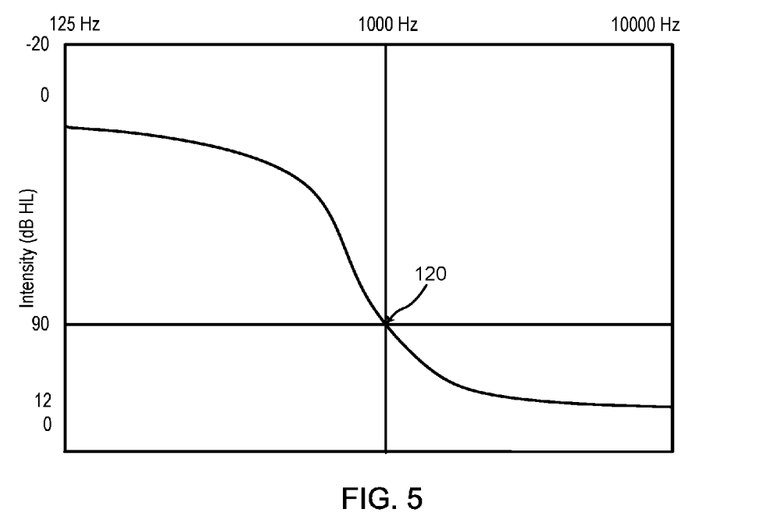
FIG. 5 illustrates an example audiogram.
Figure 6:
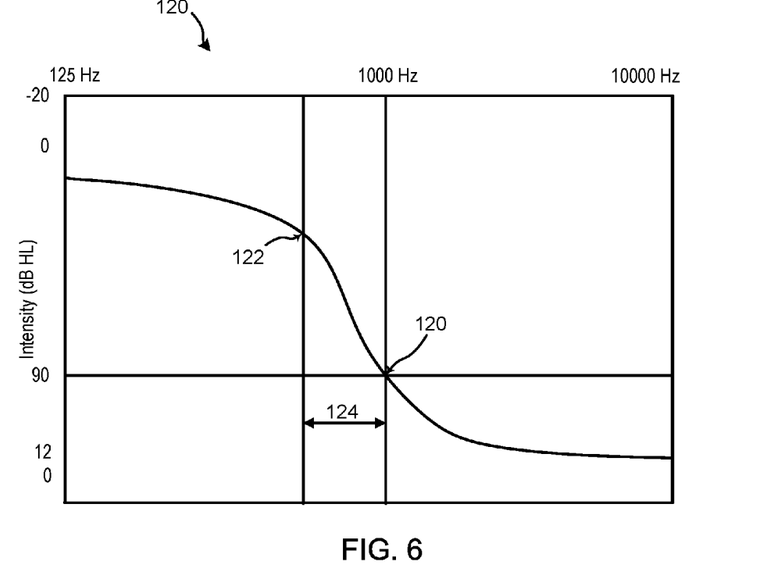
FIG. 6 illustrates another example audiogram.

FIGS. 5 and 6 illustrate example audiograms of a recipient of a hearing prosthesis system, which are referenced to further explain examples of the disclosed frequency transposition. In an example bimodal hearing prosthesis, the prosthesis includes both acoustic and electric stimulation in the same ear/cochlea. Acoustic stimulation is applied via an acoustic output for any residual hearing, and electric stimulation is applied via the cochlear implant and electrodes. The acoustic stimulation is typically dominated in the low frequencies corresponding to residual hearing and the electric stimulation takes over in the higher frequencies. The point at which the stimulation turns from acoustic to electric stimulation is known as the cross-over frequency which is made up of two cut-off frequencies (one for the acoustic path and the other for the electric path) and typically corresponds to the point at which the hearing loss exceeds 90 dB HL (although this level can be altered). At the cross-over frequency the stimulation will either be overlapping or non-overlapping. Overlapping maps are maps where there is a point in the cochlea that receives both acoustic and electric stimulation. The overlapping area can be as narrow or as wide as necessary and can include complete acoustic and electric representations (full cross-over). Non-overlapping maps are maps where there is no electric and acoustic stimulation overlapping at any point in the cochlea. These maps are set up by the audiologist in the clinic.

FIG. 5 illustrates an audiogram (e.g., a representation of the softest sounds a person can hear), with frequency/pitch on an x-axis and intensity/loudness on a y-axis. This recipient's hearing thresholds typically become greater than 90 dB HL at around 1000 Hz. This 90 dB HL hearing threshold point has conventionally been known as the cross over frequency 120 or the point above which electrical stimulation is provided, and below which acoustic stimulation is provided.

FIG. 6 illustrates the same audiogram but indicates another configuration that includes the acoustic cut off frequency 120 and an electric cut off frequency 122. In between these two frequencies is an overlapping area 124 where a hearing prosthesis may apply both acoustic and electric stimulation together. More particularly, acoustic stimulation is provided below the acoustic cut off frequency 120, and electric stimulation is provided above the electric cut off 122.

In one example, at block 104 of FIG. 4, the sound processor identifies components above the acoustic cut off frequency 120, and at block 106, the sound processor transposes the identified components above the acoustic cut off frequency to a frequency range below the cut off frequency. Then, the sound processor performs the processes of blocks 108 and/or 110, as discussed above.

In another example, at block 104 of FIG. 4, the sound processor identifies components above the electric cut off frequency 122, and at block 106, the sound processor transposes the identified components above the electric cut off frequency to a frequency range below the cut off frequency. Then, the sound processor performs the processes of blocks 108 and/or 110, as discussed above.

In yet another example, at block 104 of FIG. 4, the sound processor identifies components below the acoustic cut off frequency 122, and at block 106, the sound processor transposes the identified components below the acoustic cut off frequency to a frequency range above the cut off frequency. Then, the sound processor performs the processes of blocks 108 and/or 110, as discussed above.

In a further example, at block 104 of FIG. 4, the sound processor identifies components below the electric cut off frequency 122, and at block 106, the sound processor transposes the identified components below the electric cut off frequency to a frequency range above the cut off frequency. Then, the sound processor performs the processes of blocks 108 and/or 110, as discussed above.

Figure 7:
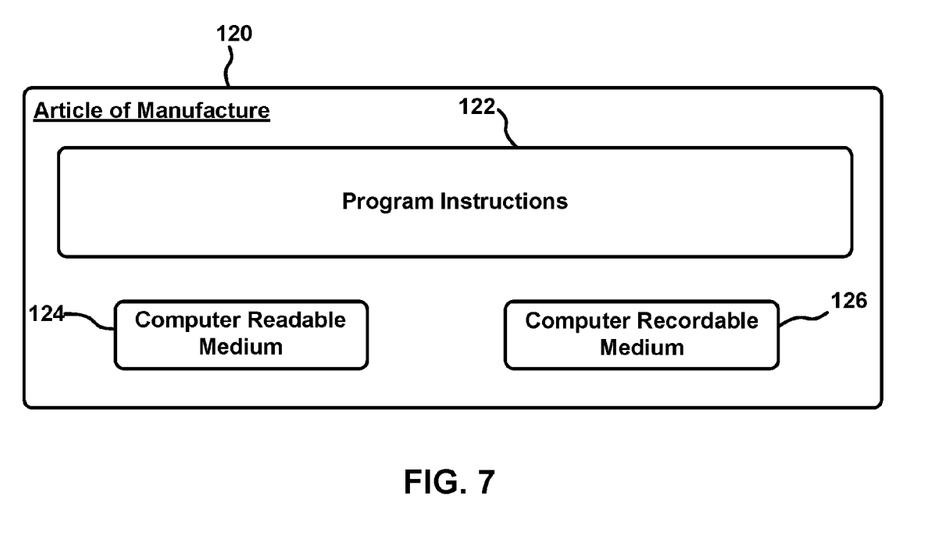
FIG. 7 is a block diagram of an article of manufacture including computer-readable media with instructions for controlling a bimodal hearing prosthesis.

FIG. 7 shows an example of an article of manufacture 120 including computer readable media with instructions 122 for adjusting parameters of a bimodal hearing prosthesis. In FIG. 7, the example article of manufacture 120 includes computer program instructions 122 for executing a computer process on a computing device, arranged according to at least some embodiments described herein, such as the methods of FIGS. 2-4.

In some examples, the article of manufacture 120 includes a computer-readable medium 124, such as, but not limited to, a hard disk drive, a Compact Disc (CD), a Digital Video Disk (DVD), a digital tape, flash memory, etc. In some implementations, the article of manufacture 120 includes a computer recordable medium 126, such as, but not limited to, a hard disk drive, a Compact Disc (CD), a Digital Video Disk (DVD), a digital tape, flash memory, etc. The one or more programming instructions 122 include, for example, computer executable and/or logic implemented instructions. In some embodiments, a computing device such as the processor 28 and/or the computing device 44, alone or in combination with one or more additional processors or computing devices, may be configured to perform certain operations, functions, or actions to implement the features and functionality of the disclosed systems and methods based at least in part on the programming instructions 122.

The following clauses are provided as further descriptions of example embodiments. Clause 1—A method comprising: receiving a sound signal that represents, at least in part, music; identifying a musical component of the sound signal, wherein the identified musical component is characterized by a definite pitch; extracting the musical component from the sound signal; and generating a stimulation signal based on the extracted musical component, wherein the stimulation signal is configured for application by a stimulator to provide an acoustic output to a recipient of a hearing prosthesis system.

Clause 2—The method according to clause 1, wherein the musical component characterized by a definite pitch is a first musical component, the stimulation signal based on the extracted first musical component is a first stimulation signal, and the stimulator that may be used to apply the first stimulation signal is a first stimulator, wherein the method further comprises: identifying a second musical component of the sound signal, wherein the identified second musical component is characterized by an indefinite pitch; extracting the second musical component from the sound signal; and generating a second stimulation signal based on the extracted second musical component, wherein the second stimulation signal is configured for application by a second stimulator to provide an electrical output from the hearing prosthesis system.

Clause 3—The method of clause 1, wherein the stimulation signal based on the extracted musical component is a first stimulation signal, and the stimulator that may be used to apply the first stimulation signal is a first stimulator, wherein the method further comprises: generating a second stimulation signal based on the whole sound signal, wherein the second stimulation signal is configured for application by a second stimulator to provide an electrical output from the hearing prosthesis system.

Clause 4—The method of clause 1, wherein the stimulation signal based on the extracted musical component is a first stimulation signal, and the stimulator that may be used to apply the first stimulation signal is a first stimulator, and wherein extracting the musical component from the sound signal generates a processed sound signal without the extracted musical component, further comprising: identifying a first portion of the processed sound signal that is below a first frequency; identifying a second portion of the processed sound signal that is above the first frequency; and generating a second stimulation signal based on the second portion of the processed signal, wherein the second stimulation signal is configured for application by a second stimulator to provide an electrical output from the hearing prosthesis system; wherein the first stimulation signal is also based on the first portion of the processed sound signal.

Clause 5—The method of clause 1, wherein identifying the musical component of the sound signal includes identifying a fundamental frequency of the sound signal, wherein the fundamental frequency has an amplitude greater than a predetermined threshold.

Clause 6—The method of clause 5, wherein identifying the musical component of the sound signal includes identifying one or more harmonic frequencies of the fundamental frequency, wherein the one or more harmonic frequencies are integer multiples of the fundamental frequency.

Clause 7—The method of clause 1, further comprising: identifying a portion of the extracted musical component that is above a first frequency; and shifting the identified portion of the extracted musical component to a frequency range below the first frequency; wherein the stimulation signal is also based on the shifted identified portion of the extracted musical component.

Clause 8—The method of clause 7, wherein shifting the identified portion of the extracted musical component to the frequency range below the first frequency includes shifting the identified portion by one or more whole octaves into the frequency range below the first frequency.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A method comprising:
   receiving a sound signal at a hearing prosthesis system configured to deliver electrical and acoustic outputs to a recipient;
   identifying a plurality of components of the sound signal, wherein the plurality of components includes a tonal component and an atonal component;
   identifying a portion of the tonal component that is above a cross-over frequency, wherein the cross-over frequency corresponds to a frequency point below which the hearing prosthesis system delivers acoustic output to the recipient and above which the hearing prosthesis system delivers electrical output to the recipient;
   shifting the identified portion of the tonal component to a frequency range below the cross-over frequency;
   generating an acoustic stimulation signal based on the shifted and identified portion of the tonal component of the sound signal, wherein the acoustic stimulation signal is configured for application by a first stimulator to provide an acoustic output from hearing prosthesis system;
   generating an electrical stimulation signal based on the atonal component of the sound signal, wherein the electrical stimulation signal is configured for application by a second stimulator to provide an electrical output from the hearing prosthesis system;
   applying, by the first stimulator, the acoustic stimulation signal to a recipient of the hearing prosthesis system; and
   applying, by the second stimulator, the electrical stimulation signal to the recipient of the hearing prosthesis system.

2. The method of claim 1, wherein the first stimulation signal is based on at least the entire tonal component of the sound signal.

3. The method of claim 1, wherein shifting the identified portion of the tonal component to the frequency range below the cross-over frequency includes shifting the identified portion by one or more whole octaves into the frequency range below the cross-over frequency.

4. The method of claim 1, further comprising:
generating the acoustic stimulation signal based on the shifted and identified portion of the tonal component of the sound signal and one or more other sound components of the sound signal.

5. The method of claim 1, wherein receiving the sound signal includes receiving the sound signal by one or more of a microphone, a wired coupling, or a wireless coupling of the hearing prosthesis system.

6. The method of claim 1, wherein the received sound signal includes a tonal component track and an atonal component track.

7. The method of claim 1, wherein the sound signal represents, at least in part, a musical composition.

8. The method of claim 1, wherein the tonal component corresponds to a first group of one or more instruments and the atonal component corresponds to a second group of one or more instruments that is different than the first group of one or more instruments.

9. The method of claim 1, wherein identifying the plurality of components of the sound signal, generating the acoustic stimulation signal, and generating the electrical stimulation signal are performed by the hearing prosthesis system in real-time in relation to receiving the sound signal.

10. The method of claim 1, further comprising:
extracting, responsive to identifying the plurality of components of the sound signal, the tonal component and the atonal component from the sound signal;
storing the extracted tonal component and the extracted atonal component; and
retrieving the stored tonal component and the stored atonal component;
wherein generating the acoustic stimulation signal is based on the retrieved tonal component, and generating the electrical stimulation is based on the retrieved atonal component.

11. The method of claim 1, further comprising:
storing the acoustic stimulation signal and the electrical stimulation signal;
retrieving the stored acoustic stimulation signal and the stored electrical stimulation signal;
applying, by the first stimulator, the retrieved acoustic stimulation signal to a recipient of the hearing prosthesis system; and
applying, by the second stimulator, the retrieved electrical stimulation signal to a recipient of the hearing prosthesis system.

12. The method of claim 1, wherein applying, by the first stimulator, the acoustic stimulation signal to a recipient of the hearing prosthesis system comprises:
delivering one or more vibrations to the recipient.

13. A device configured to deliver electrical and acoustic outputs to a recipient, comprising:
an interface configured to receive a sound signal; and
a processor coupled to the interface, wherein the processor is configured to:
identify a plurality of components of the received sound signal, wherein the plurality of components include a first component characterized by a definite pitch and a second component characterized by an indefinite pitch;
determine that the first component is above a cross-over frequency, wherein the cross-over frequency corresponds to a frequency point below which the device delivers acoustic output to the recipient and above which the device delivers electrical output to the recipient;
frequency shift the first component to a frequency range below the cross-over frequency;
generate an acoustic stimulation signal based on the first component of the sound signal to provide an acoustic output the device; and
generate an electrical stimulation signal based on the second component of the sound signal to provide an electrical output from the device.

14. The device of claim 13, further comprising memory coupled to the processor, and wherein the processor is further configured to:
extract the first component and the second component from the sound signal;
store the extracted first component and the extracted second component in the memory; and
retrieve the stored first component and the stored second component;
wherein generating the acoustic stimulation signal is based on the retrieved first component,
and generating the electric stimulation is based on the retrieved second component.

15. The device of claim 13, wherein the received sound signal includes a first track corresponding to the first component and a second track corresponding to the second component.

16. The device of claim 13, wherein the interface configured to receive the sound comprises one or more of a microphone, a wired coupling, or a wireless coupling of the device.

17. A method comprising:
receiving a sound signal at a hearing prosthesis system configured to deliver electrical and acoustic outputs to a recipient;
segregating a first tonal component of the sound signal;
determining that the first tonal component is above a cross-over frequency, wherein the cross-over frequency corresponds to a frequency point below which the hearing prosthesis system delivers acoustic output to the recipient and above which the hearing prosthesis system delivers electrical output to the recipient;
frequency shifting the first tonal component from a first frequency range above the cross-over frequency to a second frequency range below the cross-over frequency; and
generating an acoustic stimulation signal based exclusively on components of the sound signal in the second frequency range, including the first tonal component,
wherein the acoustic stimulation signal is configured for application by an acoustic stimulator to provide an acoustic output from the hearing prosthesis system.

18. The method of claim 17, wherein the first tonal component is a musical instrument.

19. The method of claim 17, further comprising:
generating an electrical stimulation signal based exclusively on components of the sound signal in the first frequency range,
wherein the electrical stimulation signal is configured for application by an electrical stimulator to provide an output from the hearing prosthesis system.

20. The method of claim 19, wherein shifting the first tonal component to the frequency range below the cross-over frequency includes shifting the first tonal component by one or more whole octaves into the frequency range below the cross-over frequency.

\* \* \* \* \*